(12) United States Patent
Magoichi et al.

(10) Patent No.: US 11,173,174 B2
(45) Date of Patent: **\*Nov. 16, 2021**

(54) DNMT INHIBITOR AS SOLID TUMOR THERAPEUTIC DRUG

(71) Applicants: OHARA PHARMACEUTICAL CO., LTD., Shiga (JP); NATIONAL CANCER CENTER, Tokyo (JP)

(72) Inventors: Sako Magoichi, Shiga (JP); Toshikazu Ushijima, Tokyo (JP); Naoko Hattori, Tokyo (JP)

(73) Assignee: Ohara Pharmaceutical Co., Ltd., Koka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/607,007

(22) PCT Filed: Apr. 24, 2018

(86) PCT No.: PCT/JP2018/016514
§ 371 (c)(1),
(2) Date: Oct. 21, 2019

(87) PCT Pub. No.: WO2018/199049
PCT Pub. Date: Nov. 1, 2018

(65) Prior Publication Data
US 2020/0061093 A1 Feb. 27, 2020

(30) Foreign Application Priority Data
Apr. 25, 2017 (JP) .............................. JP2017-085754

(51) Int. Cl.
*A61K 31/706* (2006.01)
*A61P 35/00* (2006.01)

(52) U.S. Cl.
CPC ............ *A61K 31/706* (2013.01); *A61P 35/00* (2018.01)

(58) Field of Classification Search
None
See application file for complete search history.

(56) References Cited

U.S. PATENT DOCUMENTS

| 9,670,238 B1 * | 6/2017 | Sako | ...................... A61P 35/00 |
| 2016/0193239 A1 * | 7/2016 | Baylin | ................. A61K 31/167 424/172.1 |

FOREIGN PATENT DOCUMENTS

| WO | 2011 113 173 | 9/2011 |
| WO | 2011 153 374 | 12/2011 |
| WO | 2012 166 645 | 12/2012 |

OTHER PUBLICATIONS

Kimura, et al, Studies on Nucleosides and Nucleotides. VIII. Preparation and Reactions of Triphenylphosphoranediylneuclecosides, Bull. Chem. Soc. Jpn., 3670-3677, 1980, vol. 53, No. 12.
Prakash, et al., Synthesis and Evaluation of S-Acyl-2-thioethyl Esters of Modified Nucleoside 5'-Monophosphates as Inhibitors of Hepatitis C Virus RNA Replication, J. Med. Chem, 2005, 48, 1199-1210.
WIPO, PCT International Preliminary Report on Patentability, dated Oct. 29, 2019, PCT/JP2018/016514.
Booth, et al., "Chemical Methods for Decoding Cytosine Modifications in DNA" Chemical Reviews, 2015, 115, 2240-2254.
Castillo-Aguilera, et al., "DNA Methylation Targeting: The DNMT/HMT Crosstalk Challenge" Biomolecules, 2017, 7, 3.
Lin, et al., "Dysregulated Transcriptional and Post-Translational Control of DNA Methyltransferases in Cancer," Cell & Bioscience, 2014, 4:46.
Jueliger, et al., "Efficacy and Epigenetic Interactions of Novel DNA Hypomethylating Agent Guadecitabine (SGI-110) in Preclinical Models of Hepatocellular Carcinoma," Epigenetics, 2016, vol. 11, No. 10, 709-720.
Craig, et al., "Epigenetics: A Reference Manual | Book," Caister Academic Press, Sep. 2011.
Toh, et al., "Epigenetics in Cancer Stem Cells," Molecular Cancer, 2017, 16:29.

(Continued)

*Primary Examiner* — Traviss C Mcintosh, III
(74) *Attorney, Agent, or Firm* — Emerson Thomson Bennett; Daniel A. Thomson

(57) ABSTRACT

[Problem]
To provide, in place of injected agents (such as Vidaza® and Dacogen®) clinically used as therapeutic drugs for high-risk myelodysplastic syndromes, a medicine as a therapeutic drug or a prophylactic drug for various advanced solid tumors, said medicine having high stability with respect to cytidine deaminase which is a hydrolytic metabolic enzyme, being absorbed into the body even by oral administration, and having an effect of being integrated into a nucleic acid biosynthetic route and inhibiting DNA methyltransferases, i.e., DNMTs.
[Solution]
The aforementioned problem is solved by a novel compound represented by formula (I). (In the formula, R is a hydroxyl group or a hydrogen atom, and $R^1$ and $R^2$ are each a benzyl group that may have a substituent.)

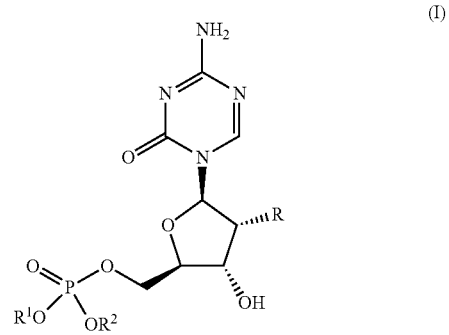

17 Claims, 2 Drawing Sheets

(56) References Cited

OTHER PUBLICATIONS

Figure 1:
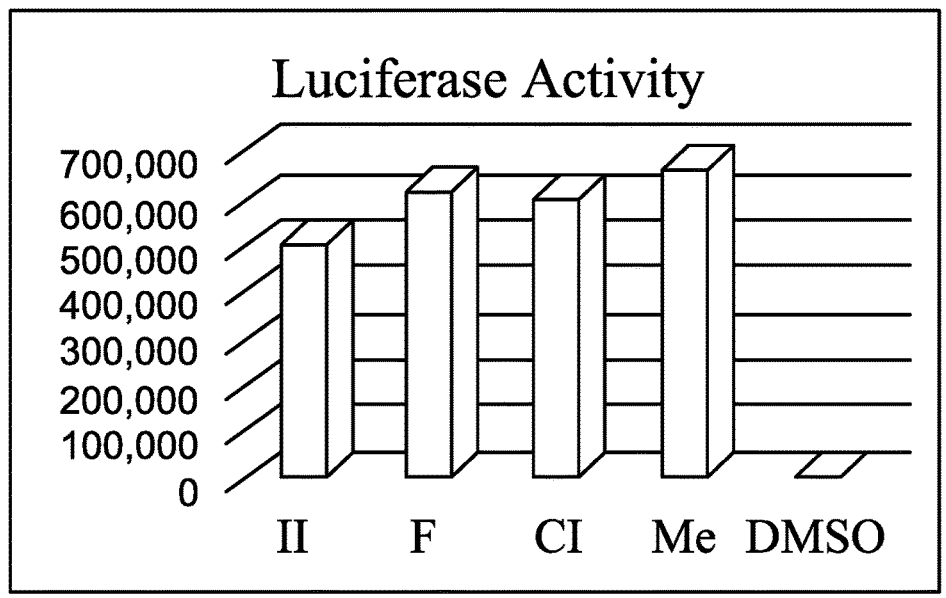
Figure 2:
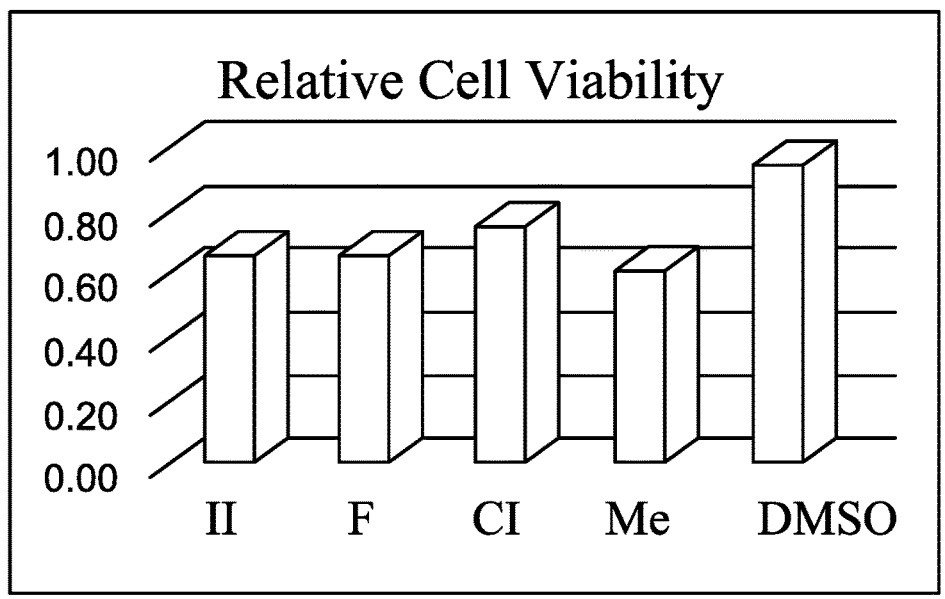
Figure 3:
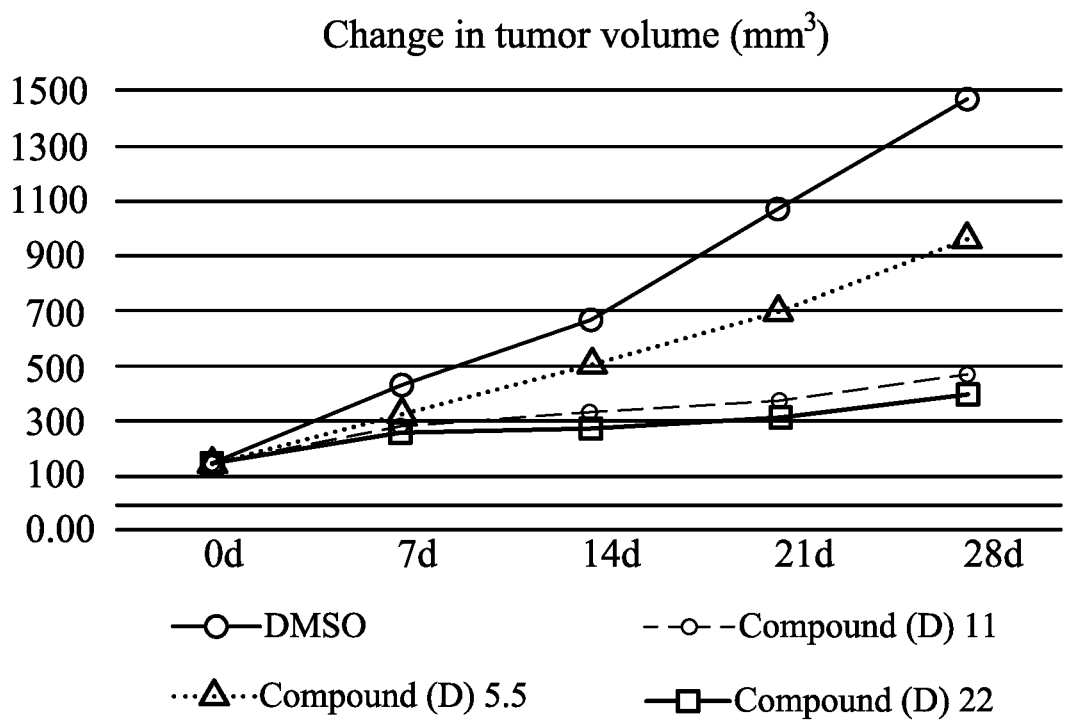
Figure 4:
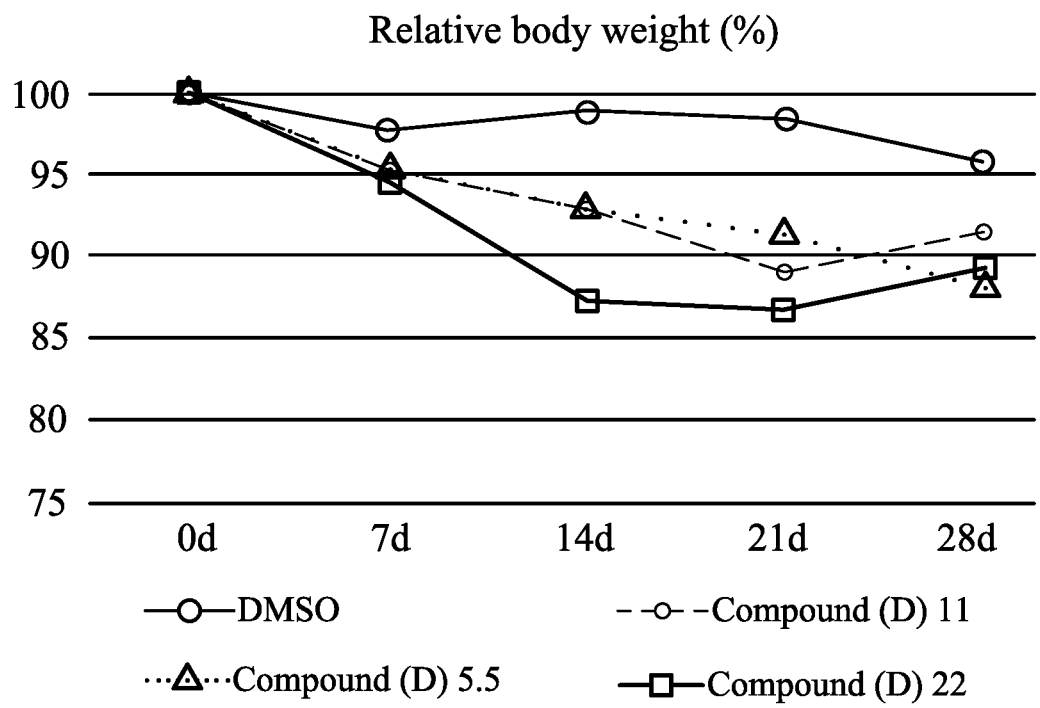

Yoshida, et al., "Epigenetic Inactivation of F AT4 Contributes to Gastric Field Cancerization," Gastric Cancer, 2017, 20:136-145.
Zielinski, et al., "Chemical Synthesis of 5-azacytidine Nucleotides and Preparation of tRNAs Containing 5-azacytidine in its 3'-terminus," Nucleic Acids Research, vol. 12, No. 12, 1984.
Ikemoto, et al., "Phosphorylation of Nucleosides with Phosphorous Oxychloride in Trialkyl Phosphate," 1995 Pharmaceutical Society of Japan, Chemical Pharmaceutical Bulletin, 43(2) 210-215.
Niwa, et al., "Prevention of Helicobacter Pylori-Induced Gastric Cancers in Gerbils by a DNA Demethylating Agent," Cancer Prevention Research, 6(4), 2013, 263-270.
Albany, et al., "Refractory Testicular Germ Cell Tumors are Highly Sensitive to the Second Generation DNA Methylation Inhibitor Guadecitabine," Oncotarget, 2017, vol. 8, (No. 2), 2949-2959.
Yoshikawa, et al., "Studies of Phosphorylation III, Selective Phosphorylation of Unprotected Nucleosides," Bulletin of the Chemical Society of Japan, 1969, vol. 42, 3505-3508.

* cited by examiner

DNMT INHIBITOR AS SOLID TUMOR THERAPEUTIC DRUG

TECHNICAL FIELD

The present invention relates to the use of a novel DNMT inhibitor which has high stability with respect to cytidine deaminase, i.e., a hydrolytic metabolic enzyme, and can be orally administered in place of 5-azacytidine and its 2'-deoxy form.

TECHNICAL BACKGROUND

DNMTs is an abbreviation for DNA-methyltransferases, which are enzymes that catalyze methylations of the amino group at 6-position of adenine ring in DNA strand (Adenine $N^6$-specific DNA-methyltransferase: EC 2.1.1.72) or the amino group at 4-position of cytosine ring (Cytosine $N^4$-specific DNA-methyltransferase: EC 2.1.1.113), and at 5-position of cytosine ring (Cytosine $C^5$-specific DNA-methyltransferase: EC 2.1.1.37). In particular, in a sequence called CpG island, which is often found in promoter region of expressed gene, the enzymes that catalyze methylation at 5-position of cytosine ring (Maintenance methyltransferase: DNMT and de novo methyltransferase: DNMT3 family) play an extremely important role in regulating normal development and cell differentiation of higher organisms (non patent documents 1 and 2).

Besides, DNMT is also deeply involved in cancer development. That is, 60-90% of all CpG islands are thought to be methylated at 5-position of cytosine ring. However, DNA methylation at abnormal levels are closely related to silencing of expressed genes. It has been clarified that the transcription and expression of a gene in which the promoter region (CpG island) is methylated at the 5-position of cytosine ring at a high level is silenced. There are two different forms of this abnormal DNA methylation compared to normal tissues, i.e., hypermethylation and hypomethylation. Hypermethylation is closely related to silencing of tumor suppressor genes. Meanwhile, extensive hypomethylation is also related to cancer development and malignancy with different mechanisms. Such silencing of expressed genes can be found, for example, in colon cancer and breast cancer, etc. non-systematically in case of tumor suppressor gene p53, in retinoblastoma and osteosarcoma, etc. in case of tumor suppressor gene Rb, and in familial breast cancer and uterine cancer, etc. in case of tumor suppressor gene BRCA1 (non patent documents 3-5).

On the other hand, cells have a mechanism wherein a methyl group is also introduced into the same 5-position of cytosine ring in a newly created DNA strand. It is also DNMT that enables this "replication of DNA methylation". Accordingly, transcription and expression of many tumor suppressor genes are inhibited to become silencing and proliferate easily in cancerous cells.

Following reaction mechanism of methylation at 5-position of cytosine ring is suggested. 5-position of cytosine ring is activated due to the attack at 6-position of cytosine ring by SH group of cysteine residue at the catalytically active center of DNMT, which facilitates methyl group to transfer from S-adenosyl-L-methionine, i.e., a methyl group donor.

As a selective enzyme inhibitor for DNMT which has such a background, 5-azacytidine and its 2'-deoxy form (Decitabine) were found and clinically used by the product names of Vidaza® and Dacogen®, respectively as therapeutic agents for high-risk myelodysplastic syndrome or acute myeloid leukemia. It is considered that since these medicines are very similar with cytosine nucleosides in chemical structure (a structure in which the carbon atom at 5-position of cytosine ring is substituted with a nitrogen atom), they are integrated into DNA in place of 2'-deoxycytidine via nucleic acid biosynthetic route to cause suicidal inhibition to the methylation reaction at 5-position of cytosine ring by DNMT in the tumor suppressor gene promoter region (CpG island), and normal expression of tumor suppressor genes is made possible, so that therapeutic effect is achieved.

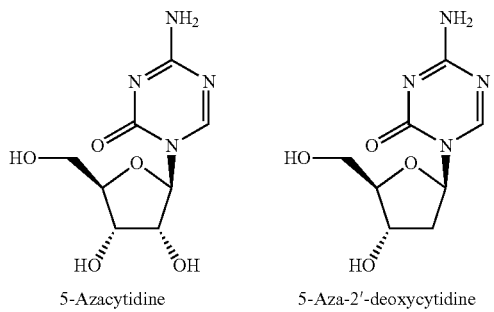 [SMILES: Nc1ncn([C@@H]2O[C@H](CO)[C@@H](O)[C@H]2O)c(=O)n1 ; Nc1ncn([C@H]2C[C@H](O)[C@@H](CO)O2)c(=O)n1]

5-Azacytidine     5-Aza-2'-deoxycytidine

Drugs with such mechanism of action should be used as anticancer agents in wide ranges. However, both compounds have the disadvantage of being easily hydrolyzed by cytidine deaminase, which is a metabolic enzyme presenting in blood or liver. Accordingly, their clinical use is limited to therapeutic drugs for high-risk myelodysplastic syndromes and acute myeloid leukemia. In addition, their dosage form is limited to injected agents due to their chemical instability. Therefore, medicines which having high stability with respect to cytidine deaminase, and can be orally administered in place of 5-azacytidine and its 2'-deoxy form are desirable.

SGI-110 (Guadecitabine), a compound which has high stability with respect to cytidine deaminase, i.e., a hydrolytic metabolic enzyme, has been found recently (patent documents 1-2) and has been developed clinically as a prodrug of 5-aza-2'-deoxycytidine. However, due to its structure of dinucleotide, the compound is too polar to penetrate cell membrane easily, which makes it unsuitable for oral administration (non patent documents 6-7).

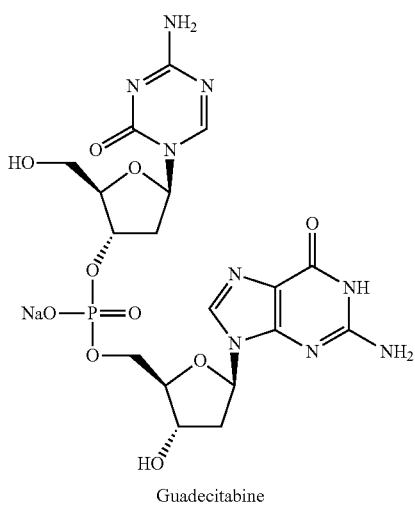

Guadecitabine

PRIOR ART DOCUMENTS

Patent Documents

1. US patent publication No. 200707279 (The specification of Japanese patent No. 5030958)
2. WO patent publication No. 2013033176 (The specification of Japanese patent No. 6038921)

Non Patent Documents

1. Chemical Reviews, 2015, vol. 115, No. 6, p. 2240-2254
2. Biomolecules, 2017, vol. 7, No. 1, p. 3
3. Epigenetics: A Reference Manual, 2011, by Craig J M, Wang N C, Kaister Academic Press
4. Cell & Bioscience, 2014, vol. 4, No. 46
5. Molecular Cancer, 2017, vol. 16, No. 29
6. Oncotarget, 2017, vol. 8, No. 2, p. 2949-2959
7. Epigenetics, 2016, vol. 11, No. 10, p. 709-720

SUMMARY OF THE INVENTION

Problems to be Solved by the Invention

An object of the present invention is to develop a compound which has high stability with respect to cytidine deaminase, i.e., a hydrolytic metabolic enzyme, and can be orally administered in place of 5-azacytidine and its 2'-deoxy form and provide not only a therapeutic drug for high-risk myelodysplastic syndromes and acute myeloid leukemia but also a therapeutic or prophylactic drug for various solid tumors (such as colorectal cancer, breast cancer, uterine cancer, stomach cancer and lung cancer).

Solutions to the Problems

In order to provide a medicine which is more useful than 5-azacytidine (Vidaza®) and its 2'-deoxy form (Dacogen®) as therapeutic drug for various bone marrow tumors, including high-risk myelodysplastic syndrome, the present inventors have earnestly undertaken studies on finding novel compounds that possess both excellent pharmacologic effects of having high stability with respect to cytidine deaminase, i.e., a hydrolytic metabolic enzyme, and being integrated easily into nucleic acid biosynthetic route in vivo and excellent physicochemical properties. Among them, the present inventors have synthesized various 5'-position dialkyl monophosphate derivatives of 5-azacytidine and its 2'-deoxy form. As a result of investigations on their chemical reactivity and biological activity, it was found out that corresponding 5'-position dibenzyl monophosphate derivatives have remarkable stability with respect to cytidine deaminase and exhibit an anti-bone marrow tumor effect. Based on these findings, the present inventors continued the investigation in details and completed the present invention.

Using a recently developed simple screening system for assessment of DNMT inhibitory activity (Epigenetics, 2016, Dec 9:0: Establishment of a high-throughput detection system for DNA demethylating agents, E. Okochi-Takada, N. Hattori et al.), various 5'-position dialkyl monophosphate derivatives of 5-azacytidine and its 2'-deoxy form were assessed. As a result, each of 5'-position dibenzyl monophosphate derivatives of 5-aza-2'-deoxycytidine was confirmed to have remarkably high DNMT inhibitory activity. It has been interpreted that these compounds are activated enzymatically or non-enzymatically in target cells and integrated into DNA via nucleic acid biosynthetic route, causing the DNMT inhibitory activity. In addition, these 5'-position dibenzyl monophosphate derivatives of 5-aza-2'-deoxycytidine are highly lipophilic, and have such physicochemical properties to allow their oral administrations. Accordingly, they were speculated to be used as orally administrable therapeutic drugs for various solid tumors related to DNMT. In addition, from the consideration of the mechanism of action (revival of tumor suppressor genes by DNMT inhibition), they were speculated to also be used as prophylactic drugs for various solid tumors related to DNMT (see Gastric Cancer, 2017, 20, 136-145 and Cancer Prevention Research, 2013, 6(4), 263-270).

Based on these findings, the present invention has solved the above problems by providing the following invention.

[1] A therapeutic or prophylactic drug for solid tumors which comprises a compound represented by formula (I), or salt thereof,

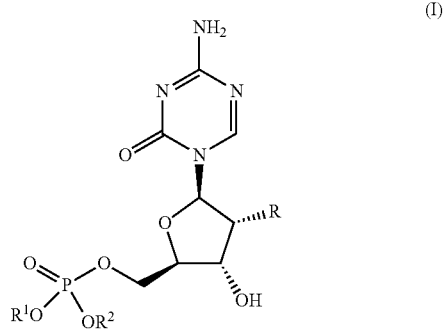

wherein, R is a hydroxyl group or a hydrogen atom, and $R^1$ and $R^2$ are the same or different and each is a benzyl group that may have a substituent.

[2] The therapeutic or prophylactic drug for solid tumors according to that described in [1], wherein each of the $R^1$ and $R^2$ is a benzyl group which may have an alkyl or a halogen atom as a substituent.

[3] The therapeutic or prophylactic drug for solid tumors according to that described in [2], wherein the alkyl is $C_1$ to $C_6$ alkyl group.

[4] The therapeutic or prophylactic drug for solid tumors according to that described in [2], wherein the alkyl is methyl group or ethyl group.

[5] The therapeutic or prophylactic drug for solid tumors according to that described in [2], wherein the halogen atom is a fluorine atom, a chlorine atom or a bromine atom.

[6] The therapeutic or prophylactic drug for solid tumors according to that described in [1], wherein the $R^1$ and $R^2$ are benzyl groups.

[7] The therapeutic or prophylactic drug for solid tumors according to any one of those described in [1] to [6], wherein the solid tumors are advanced solid tumors caused by DNMT.

Effects of the Invention

According to the present invention, it is speculated that the 5'-position dibenzyl monophosphate derivative of 5-azacytidine or its 2'-deoxy form becomes more lipophilic than the corresponding 5-azacytidine or its 2'-deoxy form, it can accordingly be orally administrated. After being absorbed in intestines, it passes through cell membrane of solid tumor cells without being affected by cytidine deaminase, i.e., a hydrolytic metabolic enzyme, in blood or liver. Then, it is hydrolyzed non-enzymatically or enzymatically in cell membrane or cells and activated. It exhibits DNMT inhibitory activity by being integrated into DNA via nucleic acid biosynthetic rout. Accordingly, it can be expected to function as a therapeutic or prophylactic drug for various solid tumors, especially advanced solid tumors caused by DNMT.

Modes to Carry Out the Invention

Terms used in the specification and claims have following meanings, unless otherwise stated.
The Compound of the Present Invention, or Salt Thereof
The compound of the present invention is represented by formula (I) as below,

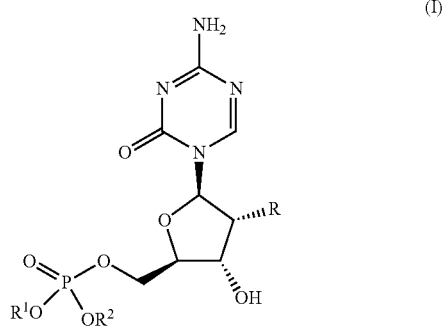

(I)

wherein, R is a hydroxyl group or a hydrogen atom, $R^1$ and $R^2$ are each a benzyl group that may have a substituent, and $R^1$ and $R^2$ may be the same or different.

Specific examples of the formula (I) include the following formulas (Ia) and (Ib).

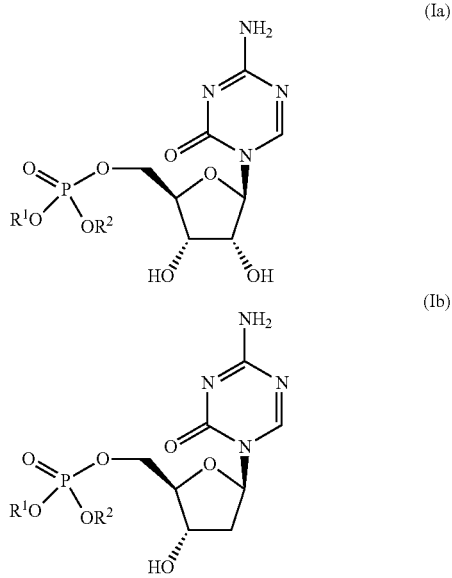

"A benzyl group that may have a substituent" refers to that it may or may not have a substituent or substituents. There may be 1 to 5 substituents, preferably 1 to 3 substituents at substitutable position of the benzyl group. When the number of substituents is 2 or more, the substituents may be the same or different. Examples of the substituents include alkyl group, halogen atom, cyano group, nitro group, and the like. Preferable examples of the substituents are alkyl group and halogen atom.

"An alkyl group" refers to, unless otherwise limited, a saturated aliphatic hydrocarbon group, such as a $C_1$ to $C_{20}$ straight or branched chains of an alkyl group or a cyclic alkyl group. Examples of the straight or branched chains of an alkyl groups include $C_1$ to $C_6$ alkyl groups, such as methyl, ethyl, propyl, iso-propyl, butyl, sec-butyl, iso-butyl, tert-butyl, pentyl, hexyl groups, and the like, heptyl, 1-methylhexyl, 5-methylhexyl, 1,1-dimethylpentyl, 2,2-dimethylpentyl, 4,4-dimethylpentyl, 1-ethylpentyl, 2-ethylpentyl, 1,1,3-trimethylbutyl, 1,2,2-trimethylbutyl, 1,3,3-trimethylbutyl, 2,2,3-trimethylbutyl, 2,3,3-trimethylbutyl, 1-propylbutyl, 1,1,2,2-tetramethylpropyl, octyl, 1-methylheptyl, 3-methylheptyl, 6-methylheptyl, 2-ethylhexyl, 5,5-dimethylhexyl, 2,4,4-trimethylpentyl, 1-ethyl-l-methylpentyl, nonyl, 1-methyloctyl, 2-methyloctyl, 3-methyloctyl, 7-methyloctyl, 1-ethylheptyl, 1,1-dimethylheptyl, 6,6-dimethylheptyl, decyl, 1-methylnonyl, 2-methylnonyl, 6-methylnonyl, 1-ethyloctyl, 1-propylheptyl, n-nonyl, n-decyl groups, and the like, preferably, $C_1$ to $C_6$ alkyl groups. Preferable examples of $C_1$ to $C_6$ alkyl groups are methyl and ethyl groups. Examples of the cyclic alkyl groups include cyclopropyl, cyclobutyl, cyclopentyl, cyclohexyl, cycloheptyl, cyclooctyl groups, and the like. In addition, preferable examples of the cyclic alkyl groups are cyclopentyl and cyclohexyl groups.

"A halogen atom" refers to a fluorine atom, a chlorine atom, a bromine atom, an iodine atom, and the like. Preferable examples are a fluorine atom, a chlorine atom and a bromine atom.

Salts of the compound represented by formula (I) of the present invention may be any salts as long as they are pharmaceutically acceptable. Their examples include, but are not limited to, acid added salts including inorganic salts (such as hydrochloride, sulfate, hydrobromide, phosphate, etc.) and organic salts (such as acetate, trifluoroacetate, succinate, maleate, fumarate, propionate, citrate, tartrate, lactate, oxalate, methane sulfonate, p-toluene sulfonate, etc.), and the like.

The compound represented by formula (I) of the present invention may be crystal, which may be in single crystalline form or a mixture of multiple crystalline forms. The crystals can be produced by crystallization according to conventional methods.

In addition, the compound represented by formula (I) of the present invention may be a solvate (for example, a hydrate and the like). Both the solvate and non-solvate (for example, a non-hydrate and the like) are included in the compound represented by formula (I).

The 5'-position dibenzyl monophosphate derivative of 5-azacytidine and its 2'-deoxy form of the present invention can be a prodrug of 5-azacytidine and its 2'-deoxy form or a prodrug of 5'-position monophosphate of 5-azacytidine and its 2'-deoxy form.

The 5'-position dibenzyl monophosphate derivative of 5-azacytidine and its 2'-deoxy form is extremely stable with respect to cytidine deaminase. It is accordingly expected to have the property of being hardly affected by cytidine deaminase, i.e., an enzyme in blood or liver, after being absorbed from gastrointestinal tract.

Having the expected high stability with respect to the above hydrolytic metabolic enzyme, the 5'-position dibenzyl monophosphate derivative of 5-azacytidine and its 2'-deoxy form according to the present invention could become a therapeutic drug or a prophylactic drug for diseases caused by DNMT.

The screening system for assessment of DNMT inhibitory activity used for 5'-position dibenzyl monophosphate derivatives of 5-azacytidine and its 2'-deoxy form is the evaluation system which we have developed recently (Epigenetics, 2016, Dec 9:0: Establishment of a high-throughput detection system for DNA demethylating agents, E. Okochi-Takada, N. Hattori et al.). It is a simple screening system for assessment of DNMT inhibitory activity which uses genetically modified colorectal cancer cells, wherein fluorescent protein luciferase can be expressed when 5-position methylation of cytosine ring in expressed gene promoter region is inhibited by inhibiting DNA methyltransferase (DNMT).

Methods for Producing the Compound Represented by Formula (I) of the Present Invention The compound of the present invention can be produced according to, for example, the following methods or other similar ones.

Method A

The compound represented by formula (I), or salt thereof can be produced according to conventional methods or their similar ones (see Bulletin of the Chemical Society, 1969, 42(12), 3505-8, Nucleic Acids Research, 1984, 12, 5025-36, Chemical & Pharmaceutical Bulletin, 1995, 43(2), 210-215 and WO-2011113173, etc.). For example, a commercially available 5-azacytidine and its 2'-deoxy form is activated by phosphorus oxychloride in a suitable solvent and then reacted with an optionally substituted benzyl alcohol in the presence of a dehydrohalogenating agent. The targeted 5'-position dibenzyl monophosphate of 5-azacytidine and its 2'-deoxy form (see formula (I)) can be obtained.

Method B

Regarding the compound represented by formula (I), or salt thereof, for example, a commercially available 5-azacytidine and its 2'-deoxy form is reacted with a dibenzyl chlorophosphate derivative in a suitable solvent in the presence of a dehydrohalogenating agent. The targeted 5'-position dibenzyl monophosphate of 5-azacytidine and its 2'-deoxy form (see formula (I)) can be obtained.

Dehydrohalogenating Agents

Examples of the dehydrohalogenating agents used include organic bases and inorganic bases. Examples of the organic bases include, but are not limited to, triethylamine, N,N-diisopropylethylamine, pyridine, 4-dimethylaminopyridine (DMAP), n-butyllithium and potassium tert-butoxide. Examples of the inorganic bases include, but are not limited to, sodium hydride, sodium carbonate, sodium bicarbonate, potassium carbonate, potassium bicarbonate and cesium carbonate. The amount of the base used is preferably 2 mol or more of the compound of starting material. Furthermore, a range of usually 2.0 to 50.0 mol, preferably the range of 5.0 to 20.0 mol, and more preferably the range of 5.0 to 10.0 mol can be exemplified with respect to 1 mol of the compound of starting material.

Solvents

From the viewpoints of smooth progress of reactions and the like, it is preferred that the reactions of the present invention are carried out in a solvent. Any solvent can be used for the reactions of the present invention as long as the reactions proceed.

Examples of the reaction solvents include phosphates such as trimethyl phosphate, triethyl phosphate, tributyl phosphate, triphenyl phosphate, tricresyl phosphate, and the like in the case of Method A, and pyridine in the case of Method B. The amount of the solvents used may be any amount as long as the reactions proceed. The amount of the solvents used in the reactions of the present invention can be adjusted appropriately by a person skilled in the art.

Reaction Temperature

Reaction temperature of the present invention is not particularly limited. In one embodiment, from the viewpoints of yield improvement, by-product control, economic efficiency, and the like, a range of −20 to 50° C. (minus 20 to plus 50° C.), preferable range of −10 to 30° C. (minus 10 to plus 30° C.), more preferable range of −10 to 20° C. (minus 10 to plus 20° C.), even more preferable range of −5 to 15° C. (minus 5 to plus 15° C.) and especially preferable range of −5 to 10° C. (minus 5 to plus 10° C.) can be mentioned as examples.

Reaction Time

Reaction time of the present invention is not particularly limited. In one embodiment, from the viewpoints of yield improvement, by-product control, economic efficiency, and the like, a range of 0.5 to 120 hours, preferable range of 1 to 72 hours, more preferable range of 1 to 48 hours, even more preferable range of 1 to 24 hours can be mentioned as examples. However, the reaction time of the present invention can be adjusted appropriately by a person skilled in the art.

Pharmaceutical Compositions of the Present Invention

The compound represented by formula (I) of the present invention can be used as a safe medicine for mammals (such as humans, monkeys, cats, pigs, horses, cattle, mice, rats, guinea pigs, dogs, rabbits, and the like) as it is or as a pharmaceutical composition mixed with pharmaceutically acceptable carriers according to conventional methods.

Regarding the said pharmaceutically acceptable carriers, various conventional organic or inorganic substances can be used as formulation materials. Examples include solid formulations, such as excipients, lubricants, binding agents, disintegrating agents, and the like; liquid formulations, such as solvents, solubilizing agents, suspending agents, tonicity agents, buffers, and the like. Furthermore, formulation additives, such as preservative agents, antioxidant agents, coloring agents, sweetening agents, and the like can also be used when necessary.

Regarding dosage forms of the pharmaceutical compositions, oral preparations such as tablets, capsules (including soft capsules and microcapsules), granules, powders, syrups, emulsions, suspensions, sustained-release preparations, and the like, can be mentioned as examples. These can be administered orally and safely. However, they are not limited to these examples, because liquid formulations are also possible.

The pharmaceutical compositions can be produced according to conventional methods in technical field of formulation, for example, the methods described in The Japanese Pharmacopeia, and the like.

Use of the Compound Represented in Formula (I) of the Present Invention

The compound represented in formula (I) of the present invention can be used in many therapeutic and prophylactic ways. In a preferable embodiment, the compound of the present invention is used for the treatment of extremely various diseases which are sensitive to the treatment with cytidines (such as Decitabine or Azacitidine). Preferred indications that can be treated using the compound of the present invention include those accompanied with undesirable or uncontrolled cell division. Such indications include various solid tumors. However, more preferably, advanced solid tumors caused by DNMT are targeted indications.

The above tumors are selected from the group consisting breast cancer, skin cancer, bone cancer, prostate cancer, liver cancer, lung cancer, brain cancer, laryngeal cancer, gallbladder cancer, pancreatic cancer, rectal cancer, parathyroid cancer, glandular tissue cancer, nerve tissue cancer, head and neck cancer, colon cancer, stomach cancer, bronchial cancer, kidney cancer, basal cell cancer, squamous cell carcinoma (both ulcer and papillary types), metastatic skin cancer, osteosarcoma, Ewing sarcoma, Venticulum cell sarcoma, myeloma, giant cell tumor, small cell lung cancer, gall cancer, islet cell tumor, primary brain tumor, acute and chronic lymphocytic and granulocytic tumors, Hairy cell tumor, adenoma, pheochromocytoma, mucosal neuroma, intestinal ganglion neuroma, hyperplastic corneal neuroma, Marfan syndrome-like constitutional tumor, Wilm tumor, seminoma, ovarian tumor, smooth muscle tumor, cervical dysplasia and cancer occurring in the above site, neuroblastoma, retinoblastoma, soft tissue sarcoma, malignant carcinoma, local skin lesions, mycosis fungoides, rhabdomyosarcoma, Kaposi sarcoma, osteogenic and other sarcomas, renal cell tumor, adenocarcinoma, multiple glioblastoma, malignant melanoma and epidermoid carcinoma.

Suitable pharmaceutical compositions used in the present invention comprise active ingredients in such effective amounts so that therapeutic and prophylactic purposes of the symptoms to be treated can be achieved.

The pharmaceutical compositions used in the present invention are provided as a dosage forms for oral administrations. The pharmaceutical compositions provided in this specification can be provided in solid, semi-solid, or liquid form for oral administrations. As used in this specification, the oral administrations also include buccal, lingual and sublingual administrations. Suitable oral dosage forms include, but are not limited to, tablets, capsules, pills, troches, medicinal candy, aroma preparations, cachets, pellets, drug-added chewing gum, granules, bulk powders, foamed formulations, or non-foamed powders or granules agents, solutions, emulsions, suspensions, solutions, wafers, sprinkles, elixirs and syrups. In addition to the active ingredient(s), the pharmaceutical compositions comprise, but not limited to, binders, fillers, diluents, disintegrants, wetting agents, lubricants, glidants, colorants, pigment migration inhibitors, sweeteners and flavoring agents. They may also comprise one or more pharmaceutically acceptable carriers or excipients.

Amounts of the compound represented by formula (I) of the present invention in pharmaceutical compositions or dosage forms may be, for example, in any one of the ranges of about 1 to 2,000 mg, about 10 to 2,000 mg, about 20 to 2,000 mg, about 50 to 1,000 mg, about 100 to 500 mg, about 150 to 500 mg, or about 150 to 250 mg.

When using the compound of the present invention as an anticancer agent, its effective dosages can be properly chosen according to character and stage of cancer, therapeutic strategy, extent of metastasis, amount of tumor, body weight, age, sex, background of genetic race of patients, and the like. However, pharmaceutically effective dosages are generally determined according to factors such as clinical observation of symptoms, stage of cancer, and the like. Daily dosage, in case of administration to human as an example, is in the range of about 0.01 to 10 mg/kg (about 0.5 to 500 mg for an adult weighing 60 kg), preferably about 0.05 to 5 mg/kg and more preferably about 0.1 to 2 mg/kg. The administration may be performed once or divided into multiple times.

EXAMPLES

Examples are provided below to further illustrate the present invention. However, the present invention is not limited in any way by them.

In following examples, room temperature refers to about 15 to 30° C.

The determinations of $^{1}$H-NMR and $^{13}$C-NMR were conducted with a JNM-ECZ 400R instrument (JEOL), in which $CDCl_3$, $DMSO-d_6$ and $CD_3OD$ were used as solvents, and chemical shifts ($\delta$) from tetramethylsilane, an internal standard, are shown in ppm.

Other terms used in the specification have the following meanings.

s: singlet;
d: doublet;
t: triplet;
m: multiplet;
br: broad;
br s: broad singlet;
J: constant of J-coupling.

In addition, mass determination of each compound was conducted with a Yamazen Smart Flash MS system.

Example 1

Activation of 5-azacytidines by phosphorus oxychloride and subsequent condensation with benzyl alcohols 122 mg of a 5-azacytidine was suspended in about 1 mL of triethyl phosphate at room temperature, added with 93 μL of phosphorus oxychloride (about 2 times mol with respect to 5-azacytidine, the starting material) while cooling at 0° C. and stirred for about 1 hour. Then, the solution was added with about 0.5 mL of a corresponding benzyl alcohol (about 10 times mol) and about 0.4 mL of pyridine (about 10 times mol) and stirred further for 1 hour while cooling at 0° C. The reaction solution was poured into a mixture of ethyl acetate-water, neutralized with dilute solution of sodium hydrogen carbonate and extracted with ethyl acetate. The extract was washed with saturated brine and dried over anhydrous magnesium sulfate. After insoluble materials were removed, the extract was concentrated to dryness under reduced pressure. An oily residue obtained was separated and purified with a silica gel column (Yamazen Smart Flash MS system). The targeted 5'-position dibenzyl monophosphate of 5-azacytidine was obtained. This is referred to as synthetic method A hereafter.

Example 2

Condensation of 5-azacytidines with dibenzyl chlorophosphate derivatives 122 mg of a 5-azacytidine was suspended in 1.0 mL of anhydrous pyridine at room temperature, added with about 0.25 mL of a corresponding dibenzyl chlorophosphate derivative (about 1.2 times mol) while cooling at 0° C. and stirred for about 1 hour. Then, the reaction solution was poured into a mixture of ethyl acetate-water, neutralized with dilute solution of sodium hydrogen carbonate, and extracted with ethyl acetate. The extract was washed with saturated brine and dried over anhydrous magnesium sulfate. After insoluble materials were removed, the extract was concentrated to dryness under reduced pressure. An oily residue obtained was separated and purified with a silica gel column (Yamazen Smart Flash MS system). The targeted 5'-position dibenzyl monophosphate of 5-azacytidine was obtained. This is referred to as synthetic method B hereafter.

The separation systems of silica gel column, separation yields, data obtained from instrumental analysis and distribution coefficients of the compounds (A) to (E) which are 5'-position dibenzyl monophosphates of 5-azacytidines synthesized according to the above synthetic methods A or B are shown as below.

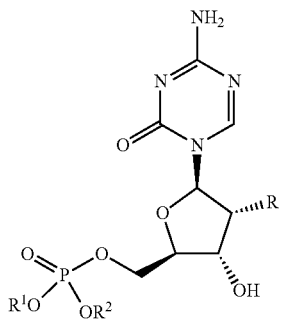

(I)

Compound (A) O,O'-Dibenzyl 5-azacytidylate (R=OH, $R^1=R^2$=Benzyl in formula (I)), (Synthetic method A), eluent system in silica gel column: chloroform/methanol, white powder, Yield=13%
Mass=505.3 (M$^+$+1): calcd. for $C_{22}H_{25}N_4O_8P$ (MW=504.14).
$^1$H-NMR (CDCl$_3$) δ: 8.32(1H, s), 8.04 (1H, br.), 7.24 (10H, br s), 7.07 (1H, br.), 5.75 (1H, br.), 4.98 and 4.96 (each 2H, each s), 4.83 (1H, br s), and 4.40-4.05 (5H, m) ppm. $^{13}$C-NMR (CDCl$_3$) δ: 165.6, 155.7, 154.5, 137.9, 135.4, 128.6, 128.4, 128.2, 128.0, 127.3, 91.5, 82.2, 74.6, 69.7 (J=4.7 Hz), 69.2, 67.4, and 66.6 ppm.
Distribution coefficient log P=0.83 (n-octanol/PBS)
Compound (B) O,O'-Dibenzyl 5-aza-2'-deoxycytidylate (R=H, $R^1=R^2$=Benzyl in formula (I)): (Synthetic methods A and B), eluent system in silica gel column: chloroform/methanol, white powder, Yield=26% (Method A), 60% (Method B)
Mass=489.3 (M$^+$+1): calcd. for $C_{22}H_{25}N_4O_7P$ (MW=488.15).
$^1$H-NMR (CD$_3$OD) δ: 8.33 (1H, s), 7.34 (10H, br s), 6.05 (1H, t, J=6.4 Hz), 5.06 and 5.03 (each 2H, each br s), 4.31-4.27 (1H, m), 4.21-4.17 (2H, m), 4.10-4.05 (1H, m), 2.41-2.36 (1H, m), and 2.15-2.06 (1H, m) ppm. $^{13}$C-NMR (CD$_3$OD) δ: 167.7, 156.9, 156.0, 139.5, 137.0(d, J=6.7 Hz), 129.8, 129.3, 129.2, 128.7, 128.4, 88.2, 86.7(d, J=7.7 Hz), 71.6, 71.0(d, J=5.8 Hz), 68.3(d, J=5.8 Hz), and 41.7 ppm.
Distribution coefficient log P=1.15 (n-octanol/PBS)
Compound (C) O,O'-Di(4-methyl)benzyl 5-aza-2'-deoxycytidylate (R=H, $R^1=R^2$=4-Methylbenzyl in formula (I)): (Synthetic method A), eluent system in silica gel column: chloroform/methanol, white powder, Yield=22%
Mass=517.3 (M$^+$+1): calcd. for $C_{24}H_{29}N_4O_7P$ (MW=516.18).
$^1$H-NMR (CD$_3$OD) δ: 8.31 (1H, s), 7.24-7.15 (8H, m), 6.03 (1H, t, J=6.0 Hz), 5.04 and 4.99 (each 2H, each br s), 4.24-4.22 (1H, m), 4.16-4.10 (2H, m), 4.10-4.05 (1H, m), 2.36-2.32 (1H, m), 2.30 (6H, br s), and 2.06-1.99 (1H, m) ppm. $^{13}$C-NMR (CD$_3$OD) δ: 167.3, 156.4, 155.6, 139.4, 138.0, 133.4 (d, J=5.8 Hz), 129.8, 129.4, 128.9, 128.1, 87.7, 86.3(d, J=7.7 Hz), 71.3, 70.5(d, J=5.8 Hz), 67.7(d, J=5.8 Hz), 41.2, and 20.7 ppm.
Compound (D) O,O'-Di(4-fluoro)benzyl 5-aza-2'-deoxycytidylate (R=H, $R^1=R^2$=4-Fluorobenzyl in formula (I)): (Synthetic method A), eluent system in silica gel column: chloroform/methanol, white powder, Yield=24%
Mass=525.2 (M$^+$+1): calcd. for $C_{22}H_{23}F_2N_4O_7P$ (MW=524.13).
$^1$H-NMR (CD$_3$OD) δ: 8.35 (1H, s), 7.39-7.01 (8H, m), 6.07 (1H, t, J=6.4 Hz), 5.06 and 5.03 (each 2H, each br s), 4.33-4.29 (1H, m), 4.28-4.17 (2H, m), 4.10-4.05 (1H, m), 2.45-2.38 (1H, m), and 2.23-2.18 (1H, m) ppm. $^{13}$C-NMR (CD$_3$OD) δ: 167.9, 157.1, 156.1, 133.1, 131.6(d, J=7.7 Hz), 130.5, 116.6, 116.4, 116.1, 116.0, 88.4, 86.8 (d, J=6.8 Hz), 71.6, 70.3(d, J=5.8 Hz), 68.4(d, J=5.8 Hz), 67.7, and 41.7 ppm.
Distribution coefficient log P=1.40 (n-octanol/PBS)
Compound (E) O,O'-Di(4-chloro)benzyl 5-aza-2'-deoxycytidylate (R=H, $R^1=R^2$=4-Chlorobenzyl in formula (I)): (Synthetic method A), eluent system in silica gel column: chloroform/methanol, white powder, Yield=20%
Mass=557.1 (M$^+$+1): calcd. for $C_{22}H_{23}C_{12}N_4O_7P$ (MW=556.07).
$^1$H-NMR (CD$_3$OD) δ: 8.34 (1H, s), 7.33 (8H, br.), 6.07 (1H, t, J=6.4 Hz), 5.06 and 5.04 (each 2H, each br s), 4.35-4.30 (1H, m), 4.28-4.17 (2H, m), 4.12-4.05 (1H, m), 2.45-2.34 (1H, m), and 2.25-2.15 (1H, m) ppm. $^{13}$C-NMR (CD$_3$OD) δ: 166.5, 155.8, 154.8, 137.0(d, J=7.7 Hz), 134.4, 133.1, 129.5, 128.7, 128.6, 128.1, 87.1, 85.4(d, J=6.8 Hz), 70.2, 68.9(d, J=5.8 Hz), 67.2(d, J=5.8 Hz), 66.3, and 40.3 ppm.
Distribution coefficient log P=2.44 (n-octanol/PBS)

Test Example 1

Stability of dibenzyl 5-azacytidylate derivatives with respect to cytidine deaminase About 1 mg of a dibenzyl 5-azacytidylate derivative (see formula (I)) obtained was dissolved in 1 mL of acetonitrile. 10 μL of the solution was added with 1 mL of PBS. 10 μL of PBS solution of cytidine deaminase was added to the solution and stirred at 37° C. for about 30 minutes to 1 hour. 1 mL of acetonitrile was added to the reaction solution and separated by centrifugation. The supernatant was analyzed with HPLC. As examples, the analytical results of Cytidine, Decitabine and O, O'-Di(4-fluoro)benzyl 5-aza-2'-deoxycytidylate (compound (D)) are shown in Table 1.

Cytidine deaminase: CDA (1-146aa), Human, His-tagged, Recombinant cytidine deaminase (ATGen)
HPLC conditions:
   Column: CAPCELL PAK ADME
     4.6 mm×150 mm, particle size: 3 μm
   Elution: eluate A=Purified water containing 10 mM ammonium formate
     eluate B=Acetonitrile
   Gradient mode: A:B=99:1→5:95/30 minutes
   Flow rate: 1.0 mL/min Oven temperature: 40° C.
   Detection: UV240 nm

TABLE 1

| Starting material | Change in HPLC pattern |
|---|---|
| Cytidine | The peak of the starting material disappeared completely after 30 minutes. |
| Decitabine | The peak of the starting material disappeared completely after 30 minutes. |
| Compound (D) | Almost no change in the peak of the starting material was confirmed even after 1 hour. |

Accordingly, it has been confirmed that the dibenzyl 5-azacytidylate derivatives according to the present invention was extremely stable with respect to cytidine deaminase. On the other hand, Cytidine and 5-Aza-2'-deoxycytidine (Decitabine) were not stable under the above reaction conditions and disappeared completely.

Test Example 2

In vivo assessment

The screening system for assessment of DNMT inhibitory activity used for 5'-position dibenzyl monophosphate derivatives of 5-azacytidine and its 2'-deoxy form is the evaluation system which we have developed recently (Epigenetics, 2016, Dec 9:0: Establishment of a high-throughput detection system for DNA demethylating agents, E. Okochi-Takada, N.

Hattori et al.). In the evaluation system, a vector in which a secretory luciferase gene was ligated in the downstream of the endogenous promoter CpG island region was introduced into colon cancer cells. When inhibitions of DNA methyltransferase (DNMT) or other DNA methylation maintenance mechanism occur, C-methylation of the promoter CpG island decreases and secretory luciferase is expressed. Since the luciferase is secretory type, it is a screening system for DNMT inhibitory activity by which the assessment can be conducted easily by collecting cell supernatant and adding the substrate of luciferin. That is, on the day before the sample addition, colon cancer cells HML58-3 that had been genetically modified were seeded in a 96-well cell culture plate. 10 μM of each sample was added to each of them, and cultured for 4 days. On day 5, the cell supernatant was collected and luciferase activity was determined. In addition, cell account for each sample was determined according to WST-8 method.

As a result, each of 5'-position dibenzyl monophosphate derivatives of 5-aza-2'-deoxycytidine (In the upper figures, H is compound (B); F is compound (D); Cl is compound (E); and Me is compound (C).) was found to have very strong luciferase activity and induce DNMT inhibition (see the upper left figure). Moreover, the cytotoxicity of these compounds was found to be low (see the upper right figure).

Test Example 3

[0055]
In vivo assessment In order to investigate the antitumor activity of 5'-position dibenzyl monophosphate derivatives of 5-azacytidine and its 2'-deoxy form, a HCT116 cell-transplanted mouse model derived from human colon cancer was used. After nurturing nude mice (female, 5 weeks old), 5×106 cells were transplanted subcutaneously into right flank. From the grouping date, samples in various concentrations (DMSO solution) were administered intraperitoneally for 6 times in total, at a frequency of twice a week. The observation was performed until the 28th day after grouping, during which body weight and tumor diameter were measured at a frequency of once a week.

As a result, regarding tumor volume, an increase suppression depending on the sample concentration was shown in comparison with the group administered with vehicle (DMSO). Regarding change in body weight, weight loss, in mild degree however, was observed in all groups.

Therefore, it has been shown that 5'-position di(4-fluoro) benzyl monophosphate derivatives of 5-aza-2'-deoxycytidine (compound (D)) (Dosage: 5.5 mg/kg, 11 mg/kg and 22 mg/kg), as an example, has dose-dependent antitumor activity against transplanted colon cancer cells and it is highly safe (see the following figures).

INDUSTRIAL APPLICABILITY

According to the present invention, a medicine which could replace clinically used 5-azacytidine and its 2'-deoxy form, and can be used as a therapeutic drug for high-risk myelodysplastic syndromes and acute myeloid leukemia and also as a therapeutic or prophylactic drug for various solid tumors caused by DNMT can be provided for clinical practice.

What is claimed is:

1. A method for treating solid tumors which comprises:
orally administering to a patient an effective dosage of a compound represented by formula (I), or salt thereof,

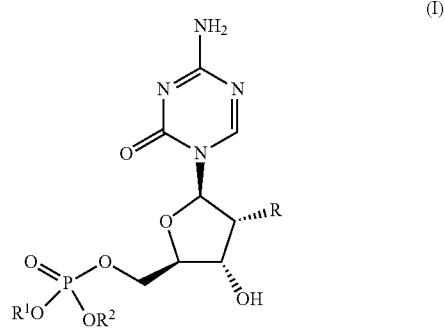

wherein, R is a hydroxyl group or a hydrogen atom, and $R^1$ and $R^2$ are the same or different and each is a benzyl group that may have a substituent.

2. The method according to claim 1, or salt thereof, wherein each of the $R^1$ and $R^2$ is a benzyl group which may have an alkyl or a halogen atom as a substituent.

3. The method according to claim 2, wherein the alkyl is $C_1$ to $C_6$ alkyl group.

4. The method according to claim 2, wherein the alkyl is methyl group or ethyl group.

5. The method according to claim 2, wherein the halogen atom is a fluorine atom, a chlorine atom or a bromine atom.

6. The method according to claim 1, wherein the $R^1$ and $R^2$ are benzyl groups.

7. The method according to claim 1, wherein the solid tumors are advanced solid tumors caused by DNMT.

8. The method according to claim 2, wherein the solid tumors are advanced solid tumors caused by DNMT.

9. The method according to claim 3, wherein the solid tumors are advanced solid tumors caused by DNMT.

10. The method according to claim 4, wherein the solid tumors are advanced solid tumors caused by DNMT.

11. The method according to claim 5, wherein the solid tumors are advanced solid tumors caused by DNMT.

12. The method according to claim 6, wherein the solid tumors are advanced solid tumors caused by DNMT.

13. The method according to claim 1, wherein R is a hydroxyl group or a hydrogen atom, and each of $R^1$ and $R^2$ is a benzyl group which may have an alkyl or a halogen atom as a substituent, and the solid tumors are selected from colorectal cancer, breast cancer, ovarian tumor, stomach cancer, renal cancer, prostate cancer, and lung cancer.

14. The method according to claim 1, wherein R is a hydroxyl group, each of the $R^1$ and $R^2$ is a benzyl group, and the solid tumors are selected from colorectal cancer, breast cancer, ovarian tumor, stomach cancer, renal cancer, prostate cancer and lung cancer.

15. The method according to claim 1, wherein R is a hydrogen atom, each of the $R^1$ and $R^2$ is a benzyl group, and the solid tumors are selected from colorectal cancer, breast cancer, ovarian tumor, stomach cancer, renal cancer, prostate cancer and lung cancer.

16. The method according to claim 14, wherein the solid tumors are advanced solid tumors caused by DNMT.

17. The method according to claim 15, wherein the solid tumors are advanced solid tumors caused by DNMT.

\* \* \* \* \*